United States Patent
Valet et al.

(10) Patent No.: US 10,426,818 B2
(45) Date of Patent: Oct. 1, 2019

(54) METHOD AND PHARMACEUTICAL COMPOSITION FOR USE IN THE TREATMENT OF DIABETES

(71) Applicants: INSERM (INSITUT NATIONAL DE LA SANTE ET DE LA RECHERCHE MEDICALE), Paris (FR); UNIVERSITE PAUL SABATIER TOULOUSE III, Toulouse (FR); CENTRE HOSPITALIER UNIVERSITAIRE DE TOULOUSE, Toulouse (FR)

(72) Inventors: Philippe Valet, Toulouse (FR); Isabelle Laurell, Toulouse (FR); Laurent Cazals, Toulouse (FR); Pierre Gourdy, Toulouse (FR)

(73) Assignees: INSERM (Institut National de la Sante et de la Recherche Medicale), Paris (FR); Universite Paul Sabatier Toulouse, Toulouse (FR); Centre Hospitalier Universitaire de Toulouse, Toulouse (FR)

( * ) Notice: Subject to any disclaimer, the term of this patent is extended or adjusted under 35 U.S.C. 154(b) by 19 days.

(21) Appl. No.: 15/560,689

(22) PCT Filed: Mar. 23, 2016

(86) PCT No.: PCT/EP2016/056383
§ 371 (c)(1),
(2) Date: Sep. 22, 2017

(87) PCT Pub. No.: WO2016/151018
PCT Pub. Date: Sep. 29, 2016

(65) Prior Publication Data
US 2018/0104306 A1    Apr. 19, 2018

(30) Foreign Application Priority Data

Mar. 24, 2015   (EP) .................................... 15305422

(51) Int. Cl.
*A61P 3/10* (2006.01)
*A61K 38/17* (2006.01)
*A61K 9/00* (2006.01)

(52) U.S. Cl.
CPC ........ *A61K 38/1709* (2013.01); *A61K 9/0019* (2013.01); *A61P 3/10* (2018.01)

(58) Field of Classification Search
None
See application file for complete search history.

(56) References Cited

U.S. PATENT DOCUMENTS

| | | | | |
|---|---|---|---|---|
| 6,492,324 B1* | 12/2002 | Hinuma | ............. | C07K 14/4702 514/3.8 |
| 2013/0196899 A1* | 8/2013 | Zecri | ........................ | C07K 7/08 514/1.9 |

FOREIGN PATENT DOCUMENTS

WO    2013/079487 A1    6/2013

OTHER PUBLICATIONS

Iturrioz et al., "Identification and pharmacological properties of E339-3D6, the first nonpeptidic apelin receptor agonist," FASEB J. 24:1506-1517 (2010).*

(Continued)

*Primary Examiner* — Julie Ha
*Assistant Examiner* — Kristina M Hellman
(74) *Attorney, Agent, or Firm* — W & C IP

(57) ABSTRACT

The present invention relates to an APJ receptor agonist for use in the treatment or the prevention of diabetes.

5 Claims, No Drawings

(56) References Cited

OTHER PUBLICATIONS

[Pyr1]-Apelin-13, PubChem accessed Feb. 2, 2019 at URL pubchem.ncbi.nlm.nih.gov/compound/_Pyr1_-Apelin-13, pp. 1-22.*
Diabetes, from http://www.merckmanuals.com/professional/endocrine-and-metabolic-disorders/ . . . , pp. 1-34, accessed Sep. 2, 2016.*
United Healthcare, diabetes, http://www.uhc.com/source4women/health_topics/diabetes/relatedinformation/d0f0417b073bf110VgnVCM1000002f10b10a_.htm—referenced Aug. 22, 2013.*
eMedicine Health, diabetes causes, http://www.onhealth.com/diabetes_health/page3.htm#diabetes_causes (referenced Aug. 22, 2013).*
U.S. National Institutes of Health: "Effect of Apelin on Insulin Sensitivity: Proof of Concept in Healthy Volunteers (APELINS)", clinicaltrials.gov, Nov. 2014.
Marana Habchi et al: "Circulating Apelin is increased in patients with type 1 or type 2 diabetes and is associated with better glycaemic control", Clinical Endocrinology, vol. 81, No. 5, pp. 696-701, Nov. 4, 2014.
Isabelle Castan-Laurell et al: "Apelin, a promising target for type 2 diabetes treatment?", Trends in Endocrinology and Metabolism, vol. 23, No. 5, pp. 234-241, May 22, 2012.
Chantal Bertrand et al: "Apelin and energy metabolism", Frontiers in Physiology, vol. 6, Apr. 10, 2015.
C. Attane et al: "Apelin Treatment Increases Complete Fatty Acid Oxidation, Mitochondrial Oxidative Capacity, and Biogenesis in Muscle of Insulin-Resistant Mice", Diabetes, vol. 61, No. 2, pp. 310-320, Feb. 1, 2012.
Anne Drougard et al: "Hypothalamic Apelin/Reactive Oxygen Species Signaling Controls Hepatic Glucose Metabolism in the Onset of Diabetes", Antioxidants & Redox Signaling, vol. 20, No. 4, pp. 557-573, Feb. 1, 2014.
Cedric Dray et al: "Apelin Stimulates Glucose Utilization in Normal and Obese Insulin-Resistant Mice", Cell Metabolism, vol. 8, No. 5, pp. 437-445, Nov. 1, 2008.
Isabelle Castan-Laurell et al: "Apelin, diabetes, and obesity", Endocrine, Springer US, Boston, vol. 40, No. 1, pp. 1-9, Jul. 2, 2011.
Chaves-Almagro C et al: "Apelin receptors: From signaling to antidiabetic strategy", European Journal of Pharmacology, vol. 763, pp. 149-159, May 22, 2015.

* cited by examiner

METHOD AND PHARMACEUTICAL COMPOSITION FOR USE IN THE TREATMENT OF DIABETES

FIELD OF THE INVENTION

The present invention relates to an APJ receptor agonist for use in the treatment or the prevention of diabetes.

BACKGROUND OF THE INVENTION

Diabetes is a disease characterized by failure of insulin feedback and secretion in the beta cells of the pancreatic islets of Langerhans and is one of the most common endocrine diseases across all age groups and populations. The most obvious metabolic effect in diabetes is chronic, erratic elevation of the blood glucose level which is associated with progressive damage to blood vessels. This may lead to heart attack, stroke, blindness, peripheral nerve dysfunction, and kidney failure. Presently there are 18.2 million people in the United States alone who have diabetes. In addition to the clinical morbidity and mortality, the economic cost of diabetes is huge, exceeding $90 billion per year in the United States alone, and the prevalence of diabetes is expected to increase.

There are two major forms of diabetes mellitus: insulin-dependent (Type I) diabetes mellitus which accounts for 5 to 10% of all cases, and non-insulin-dependent (Type-II) diabetes mellitus which comprises roughly 90 to 95% of cases.

Type I diabetes mellitus is an autoimmune disease characterized by progressive destruction of pancreatic beta-cells and most often occurring in children and young adults. The disease is associated with high rate of severe irreversible complications which occur despite the availability of insulin replacement, usually through injections administered 1-4 times daily.

Most therapeutic strategies for treatment or prevention of type I diabetes mellitus are directed to suppression of the autoimmune response in order to prevent beta-cell destruction. Accordingly, various immunosuppressive agents have been considered for preventing destruction of pancreatic beta-cells have been attempted, such as glucocorticoids, cyclophosphamide, cyclosporin A, rapamycin, FK506 and prodigiosin. However, the use of such immunosuppressive agents may cause severe side effects such as drug-related toxicity to liver or kidney and to increase incidence of infectious complications, particularly in patients with diabetes mellitus that are already susceptible to infections as part of their disease.

Type-II diabetes results from a loss of insulin production combined with body's inability to properly use insulin (insulin resistance), and is oftentimes associated with obesity and aging. In Type II diabetes, patients typically begin therapy by following a regimen of an optimal diet, weight reduction and exercise. Drug therapy is initiated when these measures no longer provide adequate metabolic control. Initial drug therapy includes: sulfonylureas (for example, tolbutamide, chlorpropamide and glibenclamide), biguanides (for example, metformin and buformin) and a-glucosidase inhibitors (for example, acarbose and voglibose). However, over 50% of all diabetics treated by presently available drugs demonstrate poor glycemic control within six years, and require insulin replacement therapy as the last resort.

Although many of the symptoms of diabetes mellitus may be controlled by insulin therapy, the long-term complications of both type I and type II diabetes mellitus are severe and may reduce life expectancy by as much as one third. Over time, elevated blood glucose levels damage blood vessels, the heart, eyes, kidneys, nerves, autonomic nervous system, skin, connective tissue, and white blood cell function.

Moreover, insulin therapy may result in insulin allergy, insulin resistance, atrophy of the subcutaneous fat at the site of insulin injection (i. e., lipoatrophy), enlargement of subcutaneous fat deposit (i. e., lipohypertrophy) due to lipogenic action of high local concentration of insulin, and insulin edema.

There is thus a widely recognized need for, and it would be highly advantageous to have new, safe and effective therapies for diabetes mellitus.

SUMMARY OF THE INVENTION

The inventors show, thanks to a translational clinical research project, that the use of apelin in humans has a positive effect on insulin sensitivity with a good tolerance and a good safety.

Thus, a first object of the invention relates to an APJ receptor agonist for use in the treatment or the prevention of diabetes.

DETAILED DESCRIPTION OF THE INVENTION

APJ Receptor Agonist and Uses Thereof

A first object of the invention relates to an APJ receptor agonist for use in the treatment or the prevention of diabetes.

As used herein, "diabetes" refers to the broad class of metabolic disorders characterized by impaired insulin production and glucose tolerance. Diabetes includes type 1 and type 2 diabetes, gestational diabetes, prediabetes, insulin resistance, metabolic syndrome, impaired fasting glycaemia and impaired glucose tolerance. Type 1 diabetes is also known as Insulin Dependent Diabetes Mellitus (IDDM). The terms are used interchangeably herein. Type 2 is also known as Non-Insulin-Dependent Diabetes Mellitus (NIDDM).

Thus, in a particular embodiment, the invention relates to an APJ receptor agonist for use in the treatment or the prevention of diabetes mellitus.

In another particular embodiment, the invention relates to an APJ receptor agonist for use in the treatment or the prevention of type 1 diabetes.

In another particular embodiment, the invention relates to an APJ receptor agonist for use in the treatment or the prevention of type 2 diabetes.

In another particular embodiment, the invention relates to an APJ receptor agonist for use in the treatment or the prevention of insulin resistance.

The term "APJ receptor" intends the receptor for apelin originally identified by O'Dowd et al. (O'Dowd et al, 1993, Gene 136: 355360).

As used herein the term "APJ receptor agonist" refers to any compound, natural or not, capable of promoting the APJ receptor function. Examples of the APJ receptor agonists of the present invention include but are not limited to polypeptides, apelinomimetics, antibodies, aptamers and small organic molecules (Apelin receptors: from signaling to antidiabetic strategy; C. Chaves-Almagro, I. Castan-Laurell, C. Dray, C. Knauf, et al; Eur J Pharmacol 2015 Sep. 22; 763(Pt B):149-59. Epub 2015 May).

Agonistic activities of a test compound toward APJ receptor may be determined by any well known method in the art. For example, since the agonist of the present invention can promote the function of the APJ receptor, the agonist can be screened using the natural agonist of APJ receptor (i.e. apelin) and its receptor. Typically, the agonist of the present invention can be obtained using the method screening the substance promoting the function of the APJ receptor, which comprises comparing (i) the case where apelin is brought in contact with the APJ receptor and (ii) the case where a test compound is brought in contact with the APJ receptor. In the screening method of the present invention, for example, (a) the binding amounts of apelin to the APJ receptor are measured (i) when apelin is brought in contact with the APJ receptor and (ii) apelin and a test compound are brought in contact with the APJ receptor; and comparing the results; or, (b) cell stimulating activities (e.g., the activities that promote arachidonic acid release, acetylcholine release, intracellular $Ca^{2+}$ release, intracellular cAMP production, intracellular cGMP production, inositol phosphate production, changes in cell membrane potential, phosphorylation of intracellular proteins, activation of c-fos, pH changes, etc.) mediated by the APJ receptor are measured (i) when apelin is brought in contact with the APJ receptor and (ii) a test compound is brought in contact with the APJ receptor; and comparing the results. Typically, the test compounds that provide a higher promotion or at least the same promotion of APJ receptor than apelin are then selected as APJ receptor agonists. Specific examples of the screening method of the present invention include: (1) a method of screening the substance promoting the function of the APJ receptor, which comprises measuring the binding amounts of labeled apelin to the APJ receptor when the labeled apelin is brought in contact with the APJ receptor and when the labeled apelin and a test compound are brought in contact with the APJ receptor; and comparing the amounts; (2) a method of screening the substance promoting the function of the APJ receptor, which comprises measuring the binding amounts of labeled apelin to a cell containing the APJ receptor or a membrane fraction of the cell, when the labeled apelin is brought in contact with the cell or membrane fraction and when the labeled apelin and a test compound are brought in contact with the cell or membrane fraction, and comparing the binding amounts; and, (3) a method of screening the substance promoting the function of the APJ receptor, which comprises measuring the binding amounts of labeled apelin to the APJ receptor expressed on a cell membrane by culturing a transformant having a DNA encoding the APJ receptor, when the labeled apelin is brought in contact with the APJ receptor and when the labeled apelin and a test compound are brought in contact with the APJ receptor, and comparing the binding amounts. In those examples, the test compounds that provide a higher binding or at least the same binding as apelin are then selected as APJ receptor agonists. Specifically, a method for determining whether a compound is an APJ receptor agonist is described in Iturrioz X. et al. (Iturrioz X, Alvear-Perez R, De Mota N, Franchet C, Guillier F, Leroux V, Dabire H, Le Jouan M, Chabane H, Gerbier R, Bonnet D, Berdeaux A, Maigret B, Galzi J L, Hibert M, Llorens-Cortes C. Identification and pharmacological properties of E339-3D6, the first nonpeptidic apelin receptor agonist. FASEB J. 2010 May; 24(5):1506-17. Epub 2009 Dec. 29). The US Patent Application Publication No US 2005/0112701 also described a test system for the identification of a ligand for angiotension receptor like-1 (APJ receptor) comprising an APJ receptor. Another method is also described in the US Patent Publication U.S. Pat. No. 6,492,324.

In one embodiment, the APJ receptor agonist is a small organic molecule. The term "small organic molecule" refers to a molecule of a size comparable to those organic molecules generally used in pharmaceuticals. The term excludes biological macromolecules (e.g., proteins, nucleic acids, etc.). Preferred small organic molecules range in size up to about 5000 Da, more preferably up to 2000 Da, and most preferably up to about 1000 Da.

Examples of small organic molecules that are APJ receptor agonists include those described in the European Patent Application Publication No EP19030052 and in Iturrioz X. et al. (Iturrioz X, Alvear-Perez R, De Mota N, Franchet C, Guillier F, Leroux V, Dabire H, Le Jouan M, Chabane H, Gerbier R, Bonnet D, Berdeaux A, Maigret B, Galzi J L, Hibert M, Llorens-Cortes C. Identification and pharmacological properties of E339-3D6, the first nonpeptidic apelin receptor agonist. FASEB J. 2010 May; 24(5):1506-17. Epub 2009 Dec. 29). Typically, a small organic molecule that is an APJ receptor agonist has the general formula (I):

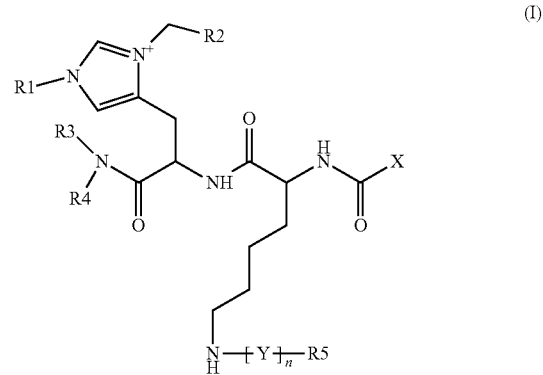

wherein:
R1 is an aryl, alkylaryl, heteroaryl or alkylheteroaryl group
R2 is a hydrogen atom or an aryl group
R3 and R4 represent a hydrogen atom or a heterocycloalkyl group providing that R3 and R4 cannot represent simultaneously a hydrogen and that R3 and R4 can both be part of a heterocycloalkyl group
R5 represents a group selected from the group consisting of boc, fmoc, texas red, patent blue V, lissamine, and rhodamine 101
n is an integer from 0 to 1
Y represents —CO—(NH)$_{n'}$-A-NH— group with:
n' is an integer from 0 to 1
A is a group selected from the group consisting of:
—(CH$_2$)$_{n''}$—
—[(CH$_2$)$_2$—O]$_{n'''}$—(CH$_2$)$_2$—
—(CH$_2$)$_m$—NH—CO—(CH$_2$)$_{m'}$—
—(CH$_2$)$_m$—NH—CO—(CH$_2$)$_{m'}$—NH—CO—(CH$_2$)$_{m''}$—
—(CH$_2$)$_m$—CO—NH—(CH$_2$)$_{m'}$—
—(CH$_2$)$_m$—CO—NH—(CH$_2$)$_{m'}$—CO—NH—(CH$_2$)$_{m''}$—
with n" representing an integer from 1 to 20
with n''' representing an integer from 1 to 10
with m, m' and m" representing independently from the other an integer from 1 to 15

X represents a group chosen in the following list:

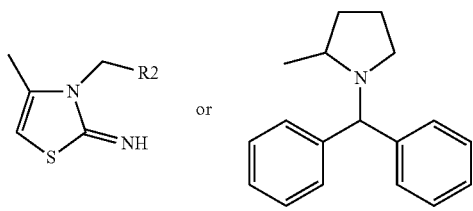

Alternatively, the APJ receptor agonist may consist in an antibody (the term including "antibody portion").

In one embodiment of the antibodies or portions thereof described herein, the antibody is a monoclonal antibody, or a portion thereof that binds to the APJ receptor. In one embodiment of the antibodies or portions thereof described herein, the antibody is a polyclonal antibody, or a portion thereof that binds to the APJ receptor. In one embodiment of the antibodies or portions thereof described herein, the antibody is a humanized antibody, or a portion thereof that binds to the APJ receptor. In one embodiment of the antibodies or portions thereof described herein, the antibody is a chimeric antibody, or a portion thereof that binds to the APJ receptor. In one embodiment of the antibodies or portions thereof described herein, the portion of the antibody comprises a light chain of the antibody. In one embodiment of the antibodies or portions thereof described herein, the portion of the antibody comprises at least a heavy chain of the antibody. In one embodiment of the antibodies or portions thereof described herein, the portion of the antibody comprises a Fab portion of the antibody. In one embodiment of the antibodies or portions thereof described herein, the portion of the antibody comprises a $F(ab')_2$ portion of the antibody. In one embodiment of the antibodies or portions thereof described herein, the portion of the antibody comprises at least a Fc portion of the antibody. In one embodiment of the antibodies or portions thereof described herein, the portion of the antibody comprises a Fv portion of the antibody. In one embodiment of the antibodies or portions thereof described herein, the portion of the antibody comprises a variable domain of the antibody. In one embodiment of the antibodies or portions thereof described herein, the portion of the antibody comprises one or more CDR domains of the antibody.

As used herein, "antibody" includes both naturally occurring and non-naturally occurring antibodies. Specifically, "antibody" includes polyclonal and monoclonal antibodies, and monovalent and divalent fragments thereof. Furthermore, "antibody" includes chimeric antibodies, wholly synthetic antibodies, single chain antibodies, and fragments thereof. The antibody may be a human or nonhuman antibody. A nonhuman antibody may be humanized by recombinant methods to reduce its immunogenicity in man.

Antibodies are prepared according to conventional methodology. Monoclonal antibodies may be generated using the method of Kohler and Milstein (Nature, 256:495, 1975). To prepare monoclonal antibodies useful in the invention, a mouse or other appropriate host animal is immunized at suitable intervals (e.g., twice-weekly, weekly, twice-monthly or monthly) with antigenic forms of APJ. The animal may be administered a final "boost" of antigen within one week of sacrifice. It is often desirable to use an immunologic adjuvant during immunization. Suitable immunologic adjuvants include Freund's complete adjuvant, Freund's incomplete adjuvant, alum, Ribi adjuvant, Hunter's Titermax, saponin adjuvants such as QS21 or Quil A, or CpG-containing immunostimulatory oligonucleotides. Other suitable adjuvants are well-known in the field. The animals may be immunized by subcutaneous, intraperitoneal, intramuscular, intravenous, intranasal or other routes. A given animal may be immunized with multiple forms of the antigen by multiple routes.

Briefly, the antigen may be provided as synthetic peptides corresponding to antigenic regions of interest in APJ. Following the immunization regimen, lymphocytes are isolated from the spleen, lymph node or other organ of the animal and fused with a suitable myeloma cell line using an agent such as polyethylene glycol to form a hydridoma. Following fusion, cells are placed in media permissive for growth of hybridomas but not the fusion partners using standard methods, as described (Coding, Monoclonal Antibodies: Principles and Practice: Production and Application of Monoclonal Antibodies in Cell Biology, Biochemistry and Immunology, 3rd edition, Academic Press, New York, 1996). Following culture of the hybridomas, cell supernatants are analyzed for the presence of antibodies of the desired specificity, i.e., that selectively bind the antigen. Suitable analytical techniques include ELISA, flow cytometry, immunoprecipitation, and western blotting. Other screening techniques are well-known in the field. Preferred techniques are those that confirm binding of antibodies to conformationally intact, natively folded antigen, such as non-denaturing ELISA, flow cytometry, and immunoprecipitation.

Significantly, as is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology*, 7th Ed., Blackwell Scientific Publications, Oxford). The Fc' and Fc regions, for example, are effectors of the complement cascade but are not involved in antigen binding. An antibody from which the pFc' region has been enzymatically cleaved, or which has been produced without the pFc' region, designated an $F(ab')_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR5). The CDRs, and in particular the CDR5 regions, and more particularly the heavy chain CDR5, are largely responsible for antibody specificity.

It is now well-established in the art that the non CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody.

This invention provides in certain embodiments compositions and methods that include humanized forms of antibodies. As used herein, "humanized" describes antibodies wherein some, most or all of the amino acids outside the CDR regions are replaced with corresponding amino acids derived from human immunoglobulin molecules. Methods of humanization include, but are not limited to, those described in U.S. Pat. Nos. 4,816,567, 5,225,539, 5,585,089, 5,693,761, 5,693,762 and 5,859,205, which are hereby incorporated by reference. The above U.S. Pat. Nos. 5,585,089 and 5,693,761, and WO 90/07861 also propose four possible criteria which may used in designing the humanized antibodies. The first proposal was that for an acceptor, use a framework from a particular human immunoglobulin that is unusually homologous to the donor immunoglobulin to be humanized, or use a consensus framework from many human antibodies. The second proposal was that if an amino acid in the framework of the human immunoglobulin is unusual and the donor amino acid at that position is typical for human sequences, then the donor amino acid rather than the acceptor may be selected. The third proposal was that in the positions immediately adjacent to the 3 CDRs in the humanized immunoglobulin chain, the donor amino acid rather than the acceptor amino acid may be selected. The fourth proposal was to use the donor amino acid reside at the framework positions at which the amino acid is predicted to have a side chain atom within 3 A of the CDRs in a three dimensional model of the antibody and is predicted to be capable of interacting with the CDRs. The above methods are merely illustrative of some of the methods that one skilled in the art could employ to make humanized antibodies. One of ordinary skill in the art will be familiar with other methods for antibody humanization.

In one embodiment of the humanized forms of the antibodies, some, most or all of the amino acids outside the CDR regions have been replaced with amino acids from human immunoglobulin molecules but where some, most or all amino acids within one or more CDR regions are unchanged. Small additions, deletions, insertions, substitutions or modifications of amino acids are permissible as long as they would not abrogate the ability of the antibody to bind a given antigen. Suitable human immunoglobulin molecules would include IgG1, IgG2, IgG3, IgG4, IgA and IgM molecules. A "humanized" antibody retains a similar antigenic specificity as the original antibody. However, using certain methods of humanization, the affinity and/or specificity of binding of the antibody may be increased using methods of "directed evolution", as described by Wu et al., J. Mol. Biol. 294:151, 1999, the contents of which are incorporated herein by reference.

Fully human monoclonal antibodies also can be prepared by immunizing mice transgenic for large portions of human immunoglobulin heavy and light chain loci. See, e.g., U.S. Pat. Nos. 5,591,669, 5,598,369, 5,545,806, 5,545,807, 6,150,584, and references cited therein, the contents of which are incorporated herein by reference. These animals have been genetically modified such that there is a functional deletion in the production of endogenous (e.g., murine) antibodies. The animals are further modified to contain all or a portion of the human germ-line immunoglobulin gene locus such that immunization of these animals will result in the production of fully human antibodies to the antigen of interest. Following immunization of these mice (e.g., XenoMouse (Abgenix), HuMAb mice (Medarex/GenPharm)), monoclonal antibodies can be prepared according to standard hybridoma technology. These monoclonal antibodies will have human immunoglobulin amino acid sequences and therefore will not provoke human anti-mouse antibody (KAMA) responses when administered to humans.

In vitro methods also exist for producing human antibodies. These include phage display technology (U.S. Pat. Nos. 5,565,332 and 5,573,905) and in vitro stimulation of human B cells (U.S. Pat. Nos. 5,229,275 and 5,567,610). The contents of these patents are incorporated herein by reference.

Thus, as will be apparent to one of ordinary skill in the art, the present invention also provides for F(ab') 2 Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')$_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

The various antibody molecules and fragments may derive from any of the commonly known immunoglobulin classes, including but not limited to IgA, secretory IgA, IgE, IgG and IgM. IgG subclasses are also well known to those in the art and include but are not limited to human IgG1, IgG2, IgG3 and IgG4.

In another embodiment, the antibody according to the invention is a single domain antibody. The term "single domain antibody" (sdAb) or "VHH" refers to the single heavy chain variable domain of antibodies of the type that can be found in Camelid mammals which are naturally devoid of light chains. Such VHH are also called "Nanobody®". According to the invention, sdAb can particularly be llama sdAb.

In another embodiment the APJ receptor agonist is an aptamer.

Aptamers are a class of molecules that represents an alternative to antibodies in term of molecular recognition. Aptamers are oligonucleotide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. and Gold L., 1990. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consists of a conformationally constrained antibody variable region displayed by a platform protein, such as E. coli Thioredoxin A that are selected from combinatorial libraries by two hybrid methods (Colas et al., 1996). Then after raising aptamers directed against APJs as above described, the skilled man in the art can easily select those promoting APJ receptor function.

In another embodiment the APJ receptor agonist may consist in a polypeptide. Preferably, said polypeptide is the apelin itself. More preferably, the polypeptide is an apelin polypeptide.

The term "apelin" has its general meaning in the art and includes naturally occurring apelin and function conservative variants and modified forms thereof. The apelin can be from any source, but typically is a mammalian (e.g., human and non-human primate) apelin, and more particularly a human apelin. The sequence of apelin protein and nucleic acids for encoding such proteins are well known to those of skill in the art. Apelin is synthesized as 77-amino acid precursor and is found as a dimer, stabilized by disulfide bridges (Lee D K, Saldivia V R, Nguyen T, Cheng R, George S R, O'Dowd B F. Modification of the terminal residue of apelin-13 antagonizes its hypotensive action. Endocrinology. January 146(1):231-6. 2005). The pre-apelin is converted by proteolytic cleavage to produce different C-terminal fragments, including apelin-36, apelin-17, apelin-13, and the post-translationally modified (Pyr$^1$)apelin-13, all are agonist to apelin receptor: APJ. The lack of cysteine residues in these C-terminal fragments suggests that the mature peptides are monomeric. It should be understood that, as those of skill in the art are aware of the sequence of these molecules, any apelin protein or gene sequence variant may be used as long as it has the properties of an apelin.

"Function conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids other than those indicated as conserved may differ in a protein so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide which has at least 60% amino acid identity as determined by BLAST or FASTA algorithms, preferably at least 75%, most preferably at least 85%, and even more preferably at least 90%, and which has the same or substantially similar properties or functions as the native or parent protein to which it is compared.

According to the invention the term "apelin" polypeptide refers to any polypeptide that comprises the apelin-13 C-terminal fragment. Accordingly, the term encompasses apelin itself or fragments thereof comprising the apelin-17 or apelin-36 fragments.

In a particular embodiment, the apelin used according to the invention is the (Pyr$^1$)apelin-13.

In specific embodiments, it is contemplated that apelin polypeptides used in the therapeutic methods of the present invention may be modified in order to improve their therapeutic efficacy. Such modification of therapeutic compounds may be used to decrease toxicity, increase circulatory time, or modify biodistribution. For example, the toxicity of potentially important therapeutic compounds can be decreased significantly by combination with a variety of drug carrier vehicles that modify biodistribution.

A strategy for improving drug viability is the utilization of water-soluble polymers. Various water-soluble polymers have been shown to modify biodistribution, improve the mode of cellular uptake, change the permeability through physiological barriers; and modify the rate of clearance from the body. To achieve either a targeting or sustained-release effect, water-soluble polymers have been synthesized that contain drug moieties as terminal groups, as part of the backbone, or as pendent groups on the polymer chain.

Polyethylene glycol (PEG) has been widely used as a drug carrier, given its high degree of biocompatibility and ease of modification. Attachment to various drugs, proteins, and liposomes has been shown to improve residence time and decrease toxicity. PEG can be coupled to active agents through the hydroxyl groups at the ends of the chain and via other chemical methods; however, PEG itself is limited to at most two active agents per molecule. In a different approach, copolymers of PEG and amino acids were explored as novel biomaterials which would retain the biocompatibility properties of PEG, but which would have the added advantage of numerous attachment points per molecule (providing greater drug loading), and which could be synthetically designed to suit a variety of applications.

Those of skill in the art are aware of PEGylation techniques for the effective modification of drugs. For example, drug delivery polymers that consist of alternating polymers of PEG and tri-functional monomers such as lysine have been used by VectraMed (Plainsboro, N.J.). The PEG chains (typically 2000 daltons or less) are linked to the a- and e-amino groups of lysine through stable urethane linkages. Such copolymers retain the desirable properties of PEG, while providing reactive pendent groups (the carboxylic acid groups of lysine) at strictly controlled and predetermined intervals along the polymer chain. The reactive pendent groups can be used for derivatization, cross-linking, or conjugation with other molecules. These polymers are useful in producing stable, long-circulating pro-drugs by varying the molecular weight of the polymer, the molecular weight of the PEG segments, and the cleavable linkage between the drug and the polymer. The molecular weight of the PEG segments affects the spacing of the drug/linking group complex and the amount of drug per molecular weight of conjugate (smaller PEG segments provides greater drug loading). In general, increasing the overall molecular weight of the block co-polymer conjugate will increase the circulatory half-life of the conjugate. Nevertheless, the conjugate must either be readily degradable or have a molecular weight below the threshold-limiting glomular filtration (e.g., less than 45 kDa).

In addition, to the polymer backbone being important in maintaining circulatory half-life, and biodistribution, linkers may be used to maintain the therapeutic agent in a pro-drug form until released from the backbone polymer by a specific trigger, typically enzyme activity in the targeted tissue. For example, this type of tissue activated drug delivery is particularly useful where delivery to a specific site of biodistribution is required and the therapeutic agent is released at or near the site of pathology Linking group libraries for use in activated drug delivery are known to those of skill in the art and may be based on enzyme kinetics, prevalence of active enzyme, and cleavage specificity of the selected disease-specific enzymes (see e.g., technologies of established by VectraMed, Plainsboro, N.J.). Such linkers may be used in modifying the apelin polypeptides described herein for therapeutic delivery.

According to the invention, apelin polypeptides may be produced by conventional automated peptide synthesis methods or by recombinant expression. General principles for designing and making proteins are well known to those of skill in the art.

Apelin polypeptides of the invention may be synthesized in solution or on a solid support in accordance with conventional techniques. Various automatic synthesizers are commercially available and can be used in accordance with known protocols. Apelin polypeptides of the invention may also be synthesized by solid-phase technology employing an exemplary peptide synthesizer such as a Model 433A from Applied Biosystems Inc. The purity of any given protein; generated through automated peptide synthesis or through recombinant methods may be determined using reverse phase HPLC analysis. Chemical authenticity of each peptide may be established by any method well known to those of skill in the art.

As an alternative to automated peptide synthesis, recombinant DNA technology may be employed wherein a nucleotide sequence which encodes a protein of choice is inserted into an expression vector, transformed or transfected into an appropriate host cell and cultivated under conditions suitable for expression as described herein below. Recombinant methods are especially preferred for producing longer polypeptides.

A variety of expression vector/host systems may be utilized to contain and express the peptide or protein coding sequence. These include but are not limited to microorganisms such as bacteria transformed with recombinant bacteriophage, plasmid or cosmid DNA expression vectors; yeast transformed with yeast expression vectors; insect cell systems infected with virus expression vectors (e.g., baculovirus); plant cell systems transfected with virus expression vectors (e.g., cauliflower mosaic virus, CaMV; tobacco mosaic virus, TMV) or transformed with bacterial expression vectors (e.g., Ti or pBR322 plasmid); or animal cell systems. Those of skill in the art are aware of various techniques for optimizing mammalian expression of proteins. Mammalian cells that are useful in recombinant protein productions include but are not limited to VERO cells, HeLa cells, Chinese hamster ovary (CHO) cell lines, COS cells (such as COS-7), W138, BHK, HepG2, 3T3, RIN, MDCK, A549, PC12, K562 and 293 cells. Exemplary protocols for the recombinant expression of the peptide substrates or fusion polypeptides in bacteria, yeast and other invertebrates are known to those of skill in the art and a briefly described herein below. Mammalian host systems for the expression of recombinant proteins also are well known to those of skill in the art. Host cell strains may be chosen for a particular ability to process the expressed protein or produce certain post-translation modifications that will be useful in providing protein activity. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO, HeLa, MDCK, 293, WI38, and the like have specific cellular machinery and characteristic mechanisms for such post-translational activities and may be chosen to ensure the correct modification and processing of the introduced, foreign protein.

In the recombinant production of the apelin polypeptides of the invention, it would be necessary to employ vectors comprising polynucleotide molecules for encoding the apelin-derived proteins. Methods of preparing such vectors as well as producing host cells transformed with such vectors are well known to those skilled in the art. The polynucleotide molecules used in such an endeavor may be joined to a vector, which generally includes a selectable marker and an origin of replication, for propagation in a host. These elements of the expression constructs are well known to those of skill in the art. Generally, the expression vectors include DNA encoding the given protein being operably linked to suitable transcriptional or translational regulatory sequences, such as those derived from a mammalian, microbial, viral, or insect genes. Examples of regulatory sequences include transcriptional promoters, operators, or enhancers, mRNA ribosomal binding sites, and appropriate sequences which control transcription and translation.

The terms "expression vector," "expression construct" or "expression cassette" are used interchangeably throughout this specification and are meant to include any type of genetic construct containing a nucleic acid coding for a gene product in which part or all of the nucleic acid encoding sequence is capable of being transcribed.

The choice of a suitable expression vector for expression of the peptides or polypeptides of the invention will of course depend upon the specific host cell to be used, and is within the skill of the ordinary artisan. Methods for the construction of mammalian expression vectors are disclosed, for example, in EP-A-0367566; and WO 91/18982.

In general, the vectors useful in the invention include, but are not limited to, plasmids, phagemids, viruses, other vehicles derived from viral or bacterial sources that have been manipulated by the insertion or incorporation of the antisense oligonucleotide, siRNA, shRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rous sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

Preferred viral vectors are based on non-cytopathic eukaryotic viruses in which non-essential genes have been replaced with the gene of interest. Non-cytopathic viruses include retroviruses (e.g., lentivirus), the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are well known in the art.

Preferred viruses for certain applications are the adenoviruses and adeno-associated (AAV) viruses, which are double-stranded DNA viruses that have already been approved for human use in gene therapy. Actually 12 different AAV serotypes (AAV1 to 12) are known, each with different tissue tropisms. Recombinant AAV are derived from the dependent parvovirus AAV2. The adeno-associated virus type 1 to 12 can be engineered to be replication deficient and is capable of infecting a wide range of cell types and species. It further has advantages such as, heat and lipid solvent stability; high transduction frequencies in cells of diverse lineages, including hemopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well known to those of skill in the art. In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pBR322, pUC18, pUC19, pRC/CMV, SV40, and pBlueScript. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intramuscular, intradermal, subcutaneous, or other routes. It may also be administered by intranasal sprays or drops, rectal suppository and orally. It may also be administered into the epidermis or a mucosal surface using a gene-gun. The plasmids may be given in an aqueous solution, dried onto gold particles or in association with another DNA delivery system including but not limited to liposomes, dendrimers, cochleate and microencapsulation.

Expression requires that appropriate signals be provided in the vectors, such as enhancers/promoters from both viral and mammalian sources that may be used to drive expression of the nucleic acids of interest in host cells. Usually, the nucleic acid being expressed is under transcriptional control of a promoter. A "promoter" refers to a DNA sequence recognized by the synthetic machinery of the cell, or introduced synthetic machinery, required to initiate the specific transcription of a gene. Nucleotide sequences are operably linked when the regulatory sequence functionally relates to the DNA encoding the protein of interest (i.e., apelin, a variant and the like). Thus, a promoter nucleotide sequence is operably linked to a given DNA sequence if the promoter nucleotide sequence directs the transcription of the sequence.

Similarly, the phrase "under transcriptional control" means that the promoter is in the correct location and orientation in relation to the nucleic acid to control RNA polymerase initiation and expression of the gene. Any promoter that will drive the expression of the nucleic acid may be used. The particular promoter employed to control the expression of a nucleic acid sequence of interest is not believed to be important, so long as it is capable of directing the expression of the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter. Common promoters include, e.g., the human cytomegalovirus (CMV) immediate early gene promoter, the SV40 early promoter, the Rous sarcoma virus long terminal repeat, [beta]-actin, rat insulin promoter, the phosphoglycerol kinase promoter and glyceraldehyde-3-phosphate dehydrogenase promoter, all of which are promoters well known and readily available to those of skill in the art, can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient to produce a recoverable yield of protein of interest. By employing a promoter with well known properties, the level and pattern of expression of the protein of interest following transfection or transformation can be optimized. Inducible promoters also may be used.

Another regulatory element that is used in protein expression is an enhancer. These are genetic elements that increase transcription from a promoter located at a distant position on the same molecule of DNA. Where an expression construct employs a cDNA insert, one will typically desire to include a polyadenylation signal sequence to effect proper polyadenylation of the gene transcript. Any polyadenylation signal sequence recognized by cells of the selected transgenic animal species is suitable for the practice of the invention, such as human or bovine growth hormone and SV40 polyadenylation signals.

Other polypeptides that can be used as APJ receptor agonists include those described in U.S. Pat. No. 6,492,324, in U.S. Pat. No. 7,635,751, in US 2010221255 or in US 2008182779.

In some embodiments, the APJ receptor agonist according to the invention is an apelinomimetic.

As used herein, the term "apelinomimetics" denotes molecules which are functionally equivalent to apelin that is to say molecules which have at least one of the biological activities of the apelin, such as, for example, hypotensive effect of apelin or plasma glucose lowering of apelin. In other words, "apelinomimetics" denotes molecules able to mimic/reproduce apelin effects.

Activities of apelinomimetics may be determined by any well known method in the art. For example, the capacity of a molecule to be an apelinomimetic may be measured by the capacity to improve insulin sensitivity and/or to decrease blood glucose like the apelin. For example, a glucose tolerance test can be used (see for example en.wikipedia.org/wiki/Glucose_tolerance_test).

In a further example, the ability of a substance to act as an apelinomimetics may be assessed through its ability to increase the Glucose Infusion Rate in vivo, during an hyperglycemic clamp procedure in the assay disclosed in the examples herein and otherwise described by DeFronzo R A et al., 1979.

A further object of the invention relates to pharmaceutical compositions comprising an APJ receptor agonist for use in the treatment or the prevention of diabetes.

Typically, the APJ receptor agonist may be combined with pharmaceutically acceptable excipients, and optionally sustained-release matrices, such as biodegradable polymers, to form therapeutic compositions.

"Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The APJ receptor agonist can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active polypeptides in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. Some variation in dosage will necessarily occur depending on the condition of the subject being treated. The person responsible for administration will, in any event, determine the appropriate dose for the individual subject.

In addition to the compounds of the invention formulated for parenteral administration, such as intravenous or intramuscular injection, other pharmaceutically acceptable forms include, e.g. tablets or other solids for oral administration; liposomal formulations; time release capsules; and any other form currently used.

A further object of the invention relates to a method for screening drugs for the prevention and treatment of diabetes comprising the steps consisting of testing a plurality of compounds for their ability to be an APJ receptor agonist, and selecting positively the compounds that are APJ receptor agonists.

Methods for determining the agonistic activities of a compound for APJ receptors are described above.

Another object of the invention relates to a method for treating diabetes comprising administering to a subject in need thereof a therapeutically effective amount of an APJ receptor agonist as described above.

In still a particular object, the APJ receptor agonist is the apelin.

In another object, the apelin is the $(Pyr^1)$apelin-13.

As used herein, the term "treating" or "treatment", denotes reversing, alleviating, inhibiting the progress of, or preventing the disorder or condition to which such term applies, or reversing, alleviating, inhibiting the progress of, or preventing one or more symptoms of the disorder or condition to which such term applies.

Determination of a therapeutically effective amount is well within the capability of those skilled in the art. For any preparation used in the methods of the invention the therapeutically effective amount or dose can be estimated initially in an animal model, such as a diabetes mice model to achieve a desired concentration. Preferably, the effective amount of an APJ receptor agonist being administered to a human subject ranges between 10 nmol/kg to 150 nmol/kg per day.

In a particular embodiment, the dose administered to the subject per day may be 10 nmol/kg, 11 nmol/kg, 12 nmol/kg, 13 nmol/kg, 14 nmol/kg, 15 nmol/kg, 16 nmol/kg, 17 nmol/kg, 18 nmol/kgv, 19 nmol/kg, 20 nmol/kg, 21 nmol/kg, 22 nmol/kg, 23 nmol/kg, 24 nmol/kg, 25 nmol/kg, 26 nmol/kg, 27 nmol/kg, 28 nmol/kg, 29 nmol/kg, 30 nmol/kg, 31 nmol/kg, 32 nmol/kg, 34 nmol/kg, 35 nmol/kg, 36 nmol/kg, 37 nmol/kg, 38 nmol/kg, 39 nmol/kg, 40 nmol/kg, 41 nmol/kg, 42 nmol/kg, 43 nmol/kg, 44 nmol/kg, 45 nmol/kg, 46 nmol/kg, 47 nmol/kg, 48 nmol/kg, 49 nmol/kg, 50 nmol/kg, 51 nmol/kg, 52 nmol/kg, 53 nmol/kg, 54 nmol/kg, 55 nmol/kg, 56 nmol/kg, 57 nmol/kg, 58 nmol/kg, 59 nmol/kg or 60 nmol/kg, 61 nmol/kg, 62 nmol/kg, 63 nmol/kg, 64 nmol/kg, 65 nmol/kg, 66 nmol/kg, 67 nmol/kg, 68 nmol/kg, 69 nmol/kg, 70 nmol/kg, 71 nmol/kg, 72 nmol/kg, 73 nmol/kg, 74 nmol/kg, 75 nmol/kg, 76 nmol/kg, 77 nmol/kg, 78 nmol/kg, 79 nmol/kg, 80 nmol/kg, 81 nmol/kg, 82 nmol/kg, 83 nmol/kg, 84 nmol/kg, 85 nmol/kg, 86 nmol/kg, 87 nmol/kg, 88 nmol/kg, 89 nmol/kg, 90 nmol/kg, 91 nmol/kg, 92 nmol/kg, 93 nmol/kg, 94 nmol/kg, 95 nmol/kg, 96 nmol/kg, 97 nmol/kg, 98 nmol/kg, 99 nmol/kg, 100 nmol/kg, 101 nmol/kg, 102 nmol/kg, 103 nmol/kg, 104 nmol/kg, 105 nmol/kg, 106 nmol/kg, 107 nmol/kg, 108 nmol/kg, 109 nmol/kg, 110 nmol/kg, 111 nmol/kg, 112 nmol/kg, 113 nmol/kg, 114 nmol/kg, 115 nmol/kg, 116 nmol/kg, 117 nmol/kg, 118 nmol/kg, 119 nmol/kg, 120 nmol/kg, 121 nmol/kg, 122 nmol/kg, 123 nmol/kg, 124 nmol/kg, 125 nmol/kg, 126 nmol/kg, 127 nmol/kg, 128 nmol/kg, 129 nmol/kg, 130 nmol/kg, 131 nmol/kg, 132 nmol/kg, 133 nmol/kg, 134 nmol/kg, 135 nmol/kg, 136 nmol/kg, 137 nmol/kg, 138 nmol/kg, 139 nmol/kg, 140 nmol/kg, 141 nmol/kg, 142 nmol/kg, 143 nmol/kg, 144 nmol/kg, 145 nmol/kg, 146 nmol/kg, 147 nmol/kg, 148 nmol/kg, 149 nmol/kg, 150 nmol/kg, 151 nmol/kg, 152 nmol/kg, 153 nmol/kg, 154 nmol/kg, 155 nmol/kg, 156 nmol/kg, 157 nmol/kg, 158 nmol/kg, 159 nmol/kg, 160 nmol/kg, 161 nmol/kg, 162 nmol/kg, 163 nmol/kg, 164 nmol/kg, 165 nmol/kg, 166 nmol/kg, 167 nmol/kg, 168 nmol/kg, 169 nmol/kg, 170 nmol/kg, 171 nmol/kg, 172 nmol/kg, 173 nmol/kg, 174 nmol/kg, 175 nmol/kg, 176 nmol/kg, 177 nmol/kg, 178 nmol/kg, 179 nmol/kg, 180 nmol/kg, 181 nmol/kg, 182 nmol/kg, 183 nmol/kg, 184 nmol/kg, 185 nmol/kg, 186 nmol/kg, 187 nmol/kg, 188 nmol/kg, 189 nmol/kg, 190 nmol/kg, 191 nmol/kg, 192 nmol/kg, 193 nmol/kg, 194 nmol/kg, 195 nmol/kg, 196 nmol/kg, 197 nmol/kg, 198 nmol/kg, 199 nmol/kg and 200 nmol/kg.

In some embodiments, the daily dose administered to the subject ranges from 10 nmol/kg to 150 nmol/kg and may be any dose ranging from 10 nmol/kg to 200 nmol/kg that is listed above.

In some embodiments, the daily dose administered to the subject ranges from 10 nmol/kg to 150 nmol/kg and may be any dose ranging from 10 nmol/kg to 150 nmol/kg that is listed above.

In some embodiments, the daily dose administered to the subject ranges from 10 nmol/kg to 60 nmol/kg and may be any dose ranging from 10 nmol/kg to 60 nmol/kg that is listed above.

In some embodiments, the daily dose administered to the subject ranges from 20 nmol/kg to 40 nmol/kg and may be any dose ranging from 20 nmol/kg to 40 nmol/kg that is listed above.

In some embodiments, the daily dose administered to the subject is about 30 nmol/kg, for example is 30 nmol/kg.

In some embodiments, the said APJ receptor agonist, e.g. apelin or (Pyr$^1$)apelin-13, is administered by the parenteral route, e.g. the intravenous route.

In the embodiments wherein the said APJ receptor agonist, e.g. apelin or (Pyr$^1$)apelin-13, is administered by the parenteral route, the daily dose may be administered by perfusing the said subject during a period of time ranging from 30 minutes to 6 hours.

In the embodiments wherein the said APJ receptor agonist, e.g. apelin or (Pyr$^1$)apelin-13, is administered by the parenteral route, the daily dose may be administered by perfusing the said subject during a period of time ranging from 60 minutes to 4 hours.

In the embodiments wherein the said APJ receptor agonist, e.g. apelin or (Pyr$^1$)apelin-13, is administered by the parenteral route, the daily dose may be administered by perfusing the said subject during a period of time ranging from 1.5 hours to 2.5 hours.

In the embodiments wherein the said APJ receptor agonist, e.g. apelin or (Pyr$^1$)apelin-13, is administered by the parenteral route, the daily dose may be administered by perfusing the said subject during a period of 2 hours.

In another particular embodiment, the dose administrated to the subject may be one time, two times, three times or four times per day, every two days, every three days, every four days, every five days, every six days, every seven days, every eight days, every nine days or every ten days.

In one embodiment the APJ receptor agonist, e.g. apelin or (Pyr$^1$)apelin-13, is administered by in a chronic way.

Accordingly, in another aspect, the invention also relates to a kit-of-part that is suitable for use in the prevention or treatment of diabetes comprising an APJ receptor agonist and an anti-diabetic drug.

Thus, in one embodiment, the invention relates to (i) an APJ receptor agonist, as defined above, and (ii) at least one anti-diabetic drug, each of (i) and (ii) as a combined preparation for simultaneous, separate or sequential use in the treatment of diabetes.

As used herein, the term "anti-diabetic drug" refers to any compound, natural or synthetic, which can reduce glucose levels in the blood and therefore is useful for preventing or treating diabetes. Typically, anti-diabetic drugs encompass (1) insulin as well as insulin analogs (for instance insulin lispro marketed by Eli Lilly as "Humalog", insulin aspart marketed by Novo Nordisk or insulin glulisine marketed by Sanofi-Aventis) or variants, (2) agents that increase the amount of insulin secreted by the pancreas (e.g. glucagon-like peptide-1 (GLP-1) receptor agonists, DPP-4 inhibitors, and sulfonylureas) (3) agents that increase the sensitivity of target organs to insulin (e.g. biguanides and thiazolidinediones), and (4) agents that decrease the rate at which glucose is absorbed from the gastrointestinal tract (e.g. alpha-glucosidase inhibitors).

In one particular embodiment, the anti-diabetic drug is insulin. Human insulin is a 51 amino acid peptide hormone produced in the islets of Langerhans in the pancreas.

In another particular embodiment, the anti-diabetic drug is an insulin analog or variant.

Human insulin has three primary amino groups: the N-terminal group of the A-chain and of the B-chain and the ε-amino group of LysB29. Several insulin analogs or variants which are substituted in one or more of these groups are known in the prior art as described in WO2007/074133. Exemplary insulin analogs that are contemplated by the invention include insulin modified at amino acid position 29 of the native human insulin B chain and optionally at other positions. For instance, a preferred analog of insulin is insulin lispro marketed by Eli Lilly as "Humalog" and described in U.S. Pat. No. 5,514,646. Such insulin analog is one wherein B28 is lysine and B29 is proline, i.e., an inversion of the native human insulin amino acid sequence at positions 28 and 29 of the B-chain.

The insulin analogs of this invention can be prepared by any of a variety of recognized peptide synthesis techniques including classical (solution) methods, solid-phase methods, semi synthetic methods and the more recently available recombinant DNA methods.

In one particular embodiment, the anti-diabetic drug is a glucagon-like peptide-1 (GLP-1) receptor agonist.

Exemplary GLP-1 receptor agonists that are contemplated by the invention include but are not limited to exenatide or specific formulations thereof, as described, for example, in WO2008061355, WO2009080024, WO2009080032, liraglutide, taspoglutide (R-1583), albiglutide, lixisenatide or those which have been disclosed in WO 98/08871, WO2005027978, WO2006037811, WO2006037810 by Novo Nordisk A/S, in WO 01/04156 by Zealand or in WO 00/34331 by Beaufour-Ipsen, pramlintide acetate (Symlin; Amylin Pharmaceuticals), inhalable GLP-1 (MKC-253 from MannKind) AVE-0010, BIM-51077 (R-1583, ITM-077), PC-DAC:exendin-4 (an exendin-4 analog which is bonded covalently to recombinant human albumin), biotinylated exendin (WO2009107900), a specific formulation of exendin-4 as described in US2009238879, CVX-73, CVX-98 and CVx-96 (GLP-1 analogs which are bonded covalently to a monoclonal antibody which has specific binding sites for the GLP-1 peptide), CNTO-736 (a GLP-1 analog which is bonded to a domain which includes the Fc portion of an antibody), PGC-GLP-1 (GLP-1 bonded to a nanocarrier), agonists or modulators, as described, for example, in D. Chen et al., Proc. Natl. Acad. Sci. USA 104 (2007) 943, those as described in WO2006124529, WO2007124461, WO2008062457, WO2008082274, WO2008101017, WO2008081418, WO2008112939, WO2008112941, WO2008113601, WO2008116294, WO2008116648, WO2008119238, WO2008148839, US2008299096, WO2008152403, WO2009030738, WO2009030771, WO2009030774, WO2009035540, WO2009058734, WO2009111700, WO2009125424, WO2009129696, WO2009149148, peptides, for example obinepitide (TM-30338), orally active GLP-1 analogs (e.g. NN9924 from Novo Nordisk), amylin receptor agonists, as described, for example, in WO2007104789, WO2009034119, analogs of the human GLP-1, as described in WO2007120899, WO2008022015, WO2008056726, chimeric pegylated peptides containing both GLP-1 and glucagon residues, as described, for example, in WO2008101017, WO2009155257, WO2009155258, glycosylated GLP-1 derivatives as described in WO2009153960, and orally active hypoglycemic ingredients.

In a particular embodiment, the GLP-1 receptor agonist is exendin-4 or exenatide.

Exendin-4 is described in the U.S. Pat. No. 5,424,286 and is a hormone found in the saliva of the Gila monster which displays biological properties similar to human glucagon-like peptide-1 (GLP-1), a regulator of glucose metabolism and insulin secretion.

Exenatide is a 39-amino-acid peptide and a synthetic version of exendin-4, which enhances glucose-dependent insulin secretion by the pancreatic β-cell and suppresses inappropriately elevated glucagon secretion.

In another embodiment, the GLP-1 receptor agonist is liraglutide.

In another particular embodiment, the anti-diabetic drug is an inhibitor of dipeptidyl peptidase-IV (DDP-4).

Exemplary inhibitors of DDP-4 that are contemplated by the invention include but are not limited to vildagliptin (LAF-237), sitagliptin (MK-0431), sitagliptin phosphate, saxagliptin (BMS-477118), GSK-823093, PSN-9301, SYR-322, SYR-619, TA-6666, TS-021, GRC-8200 (melogliptin), GW-825964X, KRP-104, DP-893, ABT-341, ABT-279 or another salt thereof, S-40010, S-40755, PF-00734200, BI-1356, PHX-1149, DSP-7238, alogliptin benzoate, linagliptin, melogliptin, carmegliptin, or those compounds as described in WO2003074500, WO2003106456, WO2004037169, WO200450658, WO2005037828, WO2005058901, WO2005012312, WO2005/012308, WO2006039325, WO2006058064, WO2006015691, WO2006015701, WO2006015699, WO2006015700, WO2006018117, WO2006099943, WO2006099941, JP2006160733, WO2006071752, WO2006065826, WO2006078676, WO2006073167, WO2006068163, WO2006085685, WO2006090915, WO2006104356, WO2006127530, WO2006111261, US2006890898, US2006803357, US2006303661, WO2007015767 (LY-2463665), WO2007024993, WO2007029086, WO2007063928, WO2007070434, WO2007071738, WO2007071576, WO2007077508, WO2007087231, WO2007097931, WO2007099385, WO2007100374, WO2007112347, WO2007112669, WO2007113226, WO2007113634, WO2007115821, WO2007116092, US2007259900, EP1852108, US2007270492, WO2007126745, WO2007136603, WO2007142253, WO2007148185, WO2008017670, US2008051452, WO2008027273, WO2008028662, WO2008029217, JP2008031064, JP2008063256, WO2008033851, WO2008040974, WO2008040995, WO2008060488, WO2008064107, WO2008066070, WO2008077597, JP2008156318, WO2008087560, WO2008089636, WO2008093960, WO2008096841, WO2008101953, WO2008118848, WO2008119005, WO2008119208, WO2008120813, WO2008121506, WO2008130151, WO2008131149, WO2009003681, WO2009014676, WO2009025784, WO2009027276, WO2009037719, WO2009068531, WO2009070314, WO2009065298, WO2009082134, WO2009082881, WO2009084497, WO2009093269, WO2009099171, WO2009099172, WO2009111239, WO2009113423, WO2009116067, US2009247532, WO2010000469, WO2010015664.

In a particular embodiment, the inhibitor of DDP-4 is sitagliptin.

It should be further noted that the inhibitor of DDP-4 may be administered in combination with metformin hydrochloride (e.g. Janumet®, a solid combination of sitagliptin phosphate with metformin hydrochloride or Eucreas®, a solid combination of vildagliptin with metformin hydrochloride).

In still another particular embodiment, the anti-diabetic drug is a GPR40 receptor agonist.

Exemplary of a GPR40 receptor agonists that are contemplated by the invention include but are not limited to those described, for example, in WO2007013689, WO2007033002, WO2007106469, US2007265332, WO2007123225, WO2007131619, WO2007131620, WO2007131621, US2007265332, WO2007131622, WO2007136572, WO2008001931, WO2008030520, WO2008030618, WO2008054674, WO2008054675, WO2008066097, US2008176912, WO2008130514, WO2009038204, WO2009039942, WO2009039943, WO2009048527, WO2009054479, WO2009058237, WO2009111056, WO2010012650, WO2011161030, WO2012004269, WO2012010413.

In a particular embodiment, the GPR40 receptor agonist is TAK-875 or AMG 837. In a further particular embodiment, the anti-diabetic drug is a thiazolidinedione, for example troglitazone, ciglitazone, pioglitazone, rosiglitazone or the compounds disclosed in WO 97/41097 by Dr. Reddy's Research Foundation, especially 5-[[4-[(3,4-dihydro-3-methyl-4-oxo-2-quinazolinylmethoxy]-phenyl]methyl]-2,4-thiazolidinedione.

In a further particular embodiment, the anti-diabetic drug is a biguanide, for example metformin or one of its salts.

Other anti-diabetic drugs that are contemplated by the invention include but are not limited to those described, for example, in US 2012/0004166.

The present invention also relates to a method for preventing or treating diabetes comprising administering to a patient in need thereof a kit-of-part comprising an APJ receptor agonist and an anti-diabetic drug.

The present invention further relates to the use of an APJ receptor agonist for enhancing the clinical efficacy of an anti-diabetic drug. As used herein, the term "enhancing the clinical efficacy" refers to an improvement of the anti-inflammatory action and/or preserving pancreatic β-cell viability and function.

The invention will be further illustrated by the following FIGURES and examples. However, these examples and FIGURES should not be interpreted in any way as limiting the scope of the present invention.

EXAMPLES

Example 1: Effect of Apelin on Insulin Sensitivity: Proof of Concept in Healthy Volunteers Material & Methods It will be described below the clinical protocol conceived for assessing the therapeutic effectiveness of a pharmaceutical composition disclosed in the present specification.

Type of Trial

This trial is a Phase 1, exploratory, monocentric, placebo-controlled, double blinded, crossover study.

Trial Population

Inclusion Criteria

Men aged 18 to 40.

BMI between 25 and 30 Kg/m$^2$ (limits excluded).

Without any known chronic disease and any ongoing drug therapy (no drugs in the 30 days preceding the inclusion visit).

Non-pathological electrocardiogram.

Resting heart rate between 50 and 80 beats per minute.

Complete Blood Count (CBC) with no significant anomaly of view of the investigator.

Liver function tests without clinically significant anomaly of view of the investigator.

Renal function tests without clinically significant anomaly of view of the investigator.

Serum electrolytes without clinically significant anomaly of view of the investigator.

Fasting blood glucose lower than 110 mg/dl.

HbA1c in the normal range (4-6%).

Good peripheral venous network (forearm and back of the hand).

Volunteer allowing his blood samples being stored in a serum bank.

Sedentary person or practicing an occasional physical activity.

Being able to sign an informed consent.

Affiliated to French National Social Insurance.

Non-Inclusion Criteria

Risk factors, treatment or electrocardiogram as recommended by ICH E14 "Clinical Evaluation of QT/QTc Interval Prolongation and Proarrhythmic Potential for Non-Antiarrhythmic Drugs"

Repeated measurement of QTc>450 ms

TdP risk factor: myocardial infarction, hypokalemia, family history of long QT syndrome Personal history of cancer.

Positive HIV serology.

Positive Hepatitis B serology.

Positive Hepatitis C serology.

Cognitive impairment or mental illness (at the decision of the investigator).

Chronic excessive alcohol consumption (consumption>30 g/day or 210 g/week).

Person under judicial protection or legal guardianship.

Subject with a blood pressure greater than 140/90 mmHg.

Smoking >10 cig/day and cannot be interrupted for 24 hours.

Subject into exclusion period from another protocol.

Trial Design

We assessed the influence of intravenous (pyr1)-Apelin-13 administrations on insulin sensitivity using the hyperinsulinemic euglycemic clamp technique developed by DeFronzo et al., 1979.

Two groups of 8 male, overweighed (BMI 25-30 kg/m$^2$) healthy volunteers were included in this study. A single 2 hours continuous intravenous (pyr1)-Apelin-13 infusion was administered to each volunteer.

The first 8 volunteers were included in the low dose group. They were perfused with a 9 nmol/kg (pyr1)-Apelin-13 dose.

The study monitoring committee then reviewed the risks with regard to safety data observed in the first 8 volunteers and any published information likely to cause a change in the estimate of the risks. The inclusion of the next 8 volunteers was allowed after written authorization of the study monitoring committee.

The next 8 volunteers were included in the high dose group. They were perfused with a 30 nmol/kg (pyr1)-Apelin-13 dose.

Each volunteer underwent two clamps spaced by 7 to 21 days: a reference clamp during which a placebo solution (perfusion solution) was perfused and an "Apelin" clamp during which a (pyr1)-Apelin-13 infusion was perfused. The sequence of administration of the tested products (placebo or apelin) was randomly determined and double blinded.

The clinical study included four visits: V1: inclusion visit V2: first clamp V3: second clamp V4 end of study visit.
Flow Chart

|  | Information | Inclusion V1 (3 to 30 days after information) | Clamp 1 V2 (V1 + 3 to 15 days) | Clamp 2 V3 (V2 + 7 to 21 days) | End of study V4 (V3 + 7 to 15 days) |
|---|---|---|---|---|---|
| Visit type | Phone call | Medical consultation | One-day hospitalisatio | One-day hospitalisation | Medical consultation |
| Witten information | Sent | ✓ | | | |
| Informed consent | | ✓ | | | |
| Clinical examination | | ✓ | ✓ | ✓ | ✓ |
| Blood test | | ✓ | ✓ | ✓ | ✓ |
| Physical examination | | ✓ | ✓ | ✓ | ✓ |
| Clamp | | | ✓ | ✓ | |
| Placebo infusion | | | According to randomisation | | |
| Apelin infusion | | | According to randomisation | | |
| Adverse events | | | ✓ | ✓ | ✓ |

Euglycemic Hyperinsulinemic Clamp Technique

Insulin (Actrapid®, NovoNordisk, Copenhagen, Denmark) was perfused for 4 hours at a constant supra-physiological rate (1 mU·Kg-1·min-1) resulting in the complete inhibition of hepatic glucose production.

Blood glucose level was measured every 5 min and maintained for 4 hours at a constant physiological value (5 mmol/l) adapting the rate of infusion of a 20% glucose solution. The Glucose infusion rate (GIR) was the main evaluation criterion, and was reported on the case report form each 5 min A first steady state was reached from the 90th to the 120th min, reflecting the "basal" insulin sensitivity of peripheral tissues of the volunteer.

From the 120th min to 240th min, a continuous perfusion of the investigational product (Apelin or placebo) was added.

A second steady state was reached from the 210th to the 240th min, reflecting the "Investigational product" insulin sensitivity of peripheral tissues of the volunteer.

Primary Endpoint

The primary endpoint (deltaGIR) was the difference between the GIR measured during the steady state ending the "investigational product" perfusion phase (GIRperfusion) and the GIR measured during the steady state ending the "basal" phase (GIRbasal).

Delta GIR=GIRperfusion−GIRbasal

GIR perfusion=mean of GIR values measured at 210, 215, 220, 225, 230, 235 and 240 min GIR basal=mean of GIR values measured at 90, 95, 100, 105, 110, 115 and 120 min Secondary Endpoints Calculation of insulin sensitivity index (Si) measured at "basal" steady state and "investigational product" steady state.

Si=$M/(G \times DeltaI)$

Along With

M=average of the seven glucose infusion rate values measured at each steady-state (basal: 90-120 min and product: 210-240 min)

G=average of 7 plasma glucose values measured at each steady-state (basal: 90-120 min and product: 210-240 min)

DeltaI=difference between fasting insulin and the average of the four plasma insulin values measured at each steady-state (assay tube serum bank collected every 10 min during the basal steady-state phases: 90-120 min and product steady-state: 210-240 min)

Variations of systolic blood pressure
Variations of diastolic blood pressure
Variations of heart rate
Recording of ECG Changes
Clinical signs of intolerance/allergy/toxicity
Plasma insulin at all sampling time
Plasma glucagon at all sampling time
Plasma apelin at all sampling time
Plasma leptin at all sampling time
Plasma adiponectin at all sampling time Statistical Considerations Sample Size To assess the primary endpoint, statistical analysis of this cross over study was based on a linear mixed model. In this exploratory study, few data was available to quantify the primary endpoint variation in humans. We hypothesized approximately a 20% increase of the glucose infusion rate at the Apelin dose causing the maximum effect on carbohydrate metabolism, namely an effect of the same order of magnitude as that observed in rodents.

According to data published by Muniyappa et al. showing that the coefficient of variation of the glucose infusion rate during an euglycemic hyperinsulinemic clamp was 0.1, and using the PASS software, for a power of 86% in a cross-over trial with an expected 20% increase of the glucose infusion rate, 8 subjects were required for each dose tested. A total of 16 subjects were therefore included in this study. This calculation was based on the following statistical references:

Julious, Steven A. 2004. 'Tutorial in Biostatistics. Sample sizes for clinical trials with Normal data.' Statistics in Medicine, 23:1921-1986.

Senn, Stephen. 2002. Cross-over Trials in Clinical Research. Second Edition. John Wiley & Sons. New York.

Based on previous studies assessing the effect of different molecules, this sample size of 8 volunteers for each selected dose seemed appropriate to highlight a significant difference on the primary endpoint.

Volunteers who early discontinue the study were replaced.

Statistical Analysis

A "per protocol" statistical analysis was performed. The description was done by group (Apelin or placebo), and group x period. Analysis of the effects "group", "period" and "interaction group x period" was based on a linear mixed model that allowed to adequately analyze the crossover design and simultaneously estimate the three aforementioned effects.

If an interaction between groups and periods is highlighted, indicating a potential carryover effect, comparisons between groups were made on the first period only. The test of the interaction period x group being less powerful, the significance level was set at 0.10. In this case, only the effect "group" was introduced in the regression model to assess the difference in effect between the two groups. While this comparison limited to the first period only limits the power of the statistical test, this comparative analysis provided indications about the apelin effect.

If no interaction between the group and period was highlighted at 0.10 significance level, the two periods were retained in the between groups comparison. In this case, the regression model taked into account the repeated data for the same volunteer (1st and 2nd period) by introducing a random effect related to the voluntary and the estimate of effect "group" is adjusted on a possible effect "period."

The results were interpreted separately for each (pyr1)-Apelin-13 dose.

The primary endpoint was analyzed according to the strategy described in the paragraph above.

The quantitative secondary endpoints were analyzed according to the same strategy as the primary endpoint.

The safety and security endpoints (clinical signs of intolerance, allergy and toxicity) were described for each group (placebo/apelin) and for each (pyr1)-Apelin-13 dose. The severity of these events was systematically reported.

Results

The clinical characteristics of overweighed healthy volunteers included in this trial were as follows: age 32.8+/−6.8 years, Body mass index 27.60±1.42 kg/m$^2$, waist circumference 99.25±4.70 cm, body fat 23.94±3.11%, fasting blood glucose 0.94±0.08 g/l, HbA1c 5.44±0.25%, total cholesterol 1.84±0.25 mg/dl, HDL cholesterol 0.46±0.06 mg/dl, LDL cholesterol 1.16±0.24 mg/dl, triglycerides 1.01±0.63 mg/dl, systolic blood pressure 119.6±8.5 mm Hg, diastolic blood pressure 73.1±7.7 mm Hg, heart rate 62.4±6.8 bpm, QTc interval 412±12 ms.

At low doses (9 nmol/kg), the apelin administration resulted in a non-significant increase in ΔGIR (difference in Glucose Infusion Rate) versus placebo (+2.21±0.54 vs +1.57±0.53+mg/kg/min, p=0.06). However, a significant improvement in insulin sensitivity was observed with a dose of 30 nmol/kg (ΔGIR: +1.72±0.47 mg/kg/min with apelin versus+0.89±0.62 mg/kg/min for placebo, p=0.03). No side effect in relation with drug administration, and especially no severe side effect, has been observed. Specifically, apelin administration did not influence heart rate, blood pressure, QTc interval.

CONCLUSION

These results demonstrate the insulin-sensitizing effect of (Pyr1)-Apelin-13 in healthy humans and open new perspectives for the research and development of therapeutic alternatives targeting insulin resistance in type 2 diabetic subjects.

REFERENCES

Throughout this application, various references describe the state of the art to which this invention pertains. The disclosures of these references are hereby incorporated by reference into the present disclosure.

DeFronzo R A, Tobin J D, Andres R. Glucose clamp technique: a method for quantifying insulin secretion and resistance. Am J Physiol. 1979, 237(3):E214-23.

Muniyappa R, Lee S, Chen H, Quon M J. Current approaches for assessing insulin sensitivity and resistance in vivo: advantages, limitations, and appropriate usage. Am J Physiol Endocrinol Metab. 2008, 294(1):E15-26.

The invention claimed is:

1. A method for treating type 2 diabetes comprising administering to a human subject in need thereof a therapeutically effective amount of (Pyr1)-apelin-13.

2. The method of claim 1, wherein the therapeutically effective amount ranges from 10 nmol/kg to 200 nmol/kg per day.

3. The method of claim 2, wherein the therapeutically effective amount ranges from 20 nmol/kg to 40 nmol/kg per day.

4. The method of claim 3, wherein the therapeutically effective amount is 30 nmol/kg per day.

5. The method of claim 1, wherein the (Pyr1)apelin-13 is administered to the subject intravenously.

* * * * *